(12) United States Patent
Kaforey et al.

(10) Patent No.: US 10,842,206 B2
(45) Date of Patent: Nov. 24, 2020

(54) PATIENT PROTECTION SYSTEM CONFIGURED TO PROTECT THE HEAD OF A PATIENT

(71) Applicant: Xodus Medical, Inc., New Kensington, PA (US)

(72) Inventors: Craig Kaforey, Allison Park, PA (US); Mark Kaforey, Murrysville, PA (US); Paul Lloyd, Pittsburgh, PA (US)

(73) Assignee: Xodus Medical, Inc., New Kensington, PA (US)

( * ) Notice: Subject to any disclaimer, the term of this patent is extended or adjusted under 35 U.S.C. 154(b) by 483 days.

(21) Appl. No.: 15/019,454

(22) Filed: Feb. 9, 2016

(65) Prior Publication Data

US 2016/0150837 A1 Jun. 2, 2016

Related U.S. Application Data

(63) Continuation-in-part of application No. 14/205,520, filed on Mar. 12, 2014.

(60) Provisional application No. 62/113,825, filed on Feb. 9, 2015, provisional application No. 62/156,583, filed on May 4, 2015, provisional application No. 61/793,874, filed on Mar. 15, 2013.

(51) Int. Cl.
| | | |
|---|---|---|
| *A41D 13/11* | (2006.01) |
| *A61G 13/12* | (2006.01) |
| *A61B 34/30* | (2016.01) |
| *A61B 90/00* | (2016.01) |
| *A61B 46/00* | (2016.01) |
| *A61B 90/18* | (2016.01) |

(52) U.S. Cl.
CPC ...... *A41D 13/1107* (2013.01); *A41D 13/1161* (2013.01); *A41D 13/1184* (2013.01); *A61B 34/30* (2016.02); *A61G 13/121* (2013.01); *A61B 46/00* (2016.02); *A61B 90/18* (2016.02); *A61B 2090/08021* (2016.02)

(58) Field of Classification Search
CPC ...... A61G 13/12; A61G 13/121; A61B 34/30; A61B 2090/08021; A61B 890/18; A41D 13/1107; A41D 13/1161; A41D 13/1184
USPC .......................... 128/857, 846, 845; 2/9, 410
See application file for complete search history.

(56) References Cited

U.S. PATENT DOCUMENTS

| | | | |
|---|---|---|---|
| 4,122,847 A * | 10/1978 | Craig | ...................... A61F 9/026 |
| | | | 128/858 |
| 4,209,473 A | 6/1980 | Coyne | |
| 4,220,730 A | 9/1980 | Coyne | |

(Continued)

FOREIGN PATENT DOCUMENTS

WO 2013106426 A2 7/2013

*Primary Examiner* — Kari K Rodriquez
*Assistant Examiner* — Caitlin A Carreiro
(74) *Attorney, Agent, or Firm* — The Webb Law Firm

(57) ABSTRACT

A patient protection system and method for using the same includes a face mask structure configured to protect the head of a patient during surgical procedures. The face mask structure includes a foam body having an exterior surface and an interior surface configured to be oriented towards the patient's face to cover the patient's face during the surgical procedure; and at least one foam pad positioned on the interior surface of the face mask structure and configured to contact the patient's face during the surgical procedure. The face mask structure and the at least one foam pad are manufactured from different types of foam.

21 Claims, 23 Drawing Sheets

(56) References Cited

U.S. PATENT DOCUMENTS

| | | | |
|---|---|---|---|
| 4,574,105 A | 3/1986 | Donovan | |
| 4,719,039 A | 1/1988 | Leonardi | |
| 4,877,814 A | 10/1989 | Ito | |
| 5,180,751 A | 1/1993 | Park et al. | |
| 5,206,082 A | 4/1993 | Malone | |
| 5,527,573 A | 6/1996 | Park et al. | |
| 5,567,742 A | 10/1996 | Park | |
| 5,613,501 A * | 3/1997 | Michelson | A61F 5/3707 5/637 |
| 6,112,333 A | 9/2000 | Mazzei | |
| 6,245,266 B1 | 6/2001 | Ramesh et al. | |
| 6,453,476 B1 | 9/2002 | Moore, III | |
| 6,490,737 B1 * | 12/2002 | Mazzei | A61G 13/12 128/846 |
| 6,637,058 B1 * | 10/2003 | Lamb | A61G 13/12 5/638 |
| 6,773,796 B1 | 8/2004 | Di Cesare et al. | |
| 6,895,619 B1 | 5/2005 | Lee | |
| 7,078,443 B2 | 7/2006 | Milliren | |
| 7,360,543 B1 | 4/2008 | Coleman et al. | |
| 7,426,763 B2 | 9/2008 | Mazzei et al. | |
| 7,574,159 B2 * | 8/2009 | Choi | G03G 21/06 399/128 |
| 7,574,759 B2 * | 8/2009 | Wilson | A61G 13/009 5/622 |
| 7,748,387 B1 | 7/2010 | Vu et al. | |
| 7,759,404 B2 | 7/2010 | Burgun et al. | |
| 7,789,461 B2 | 9/2010 | Leeds | |
| 7,799,841 B2 | 9/2010 | Stadlbauer et al. | |
| 7,850,630 B1 | 12/2010 | Vu et al. | |
| 7,984,715 B2 | 7/2011 | Moyers | |
| 8,001,970 B2 | 8/2011 | King et al. | |
| 8,066,524 B2 | 11/2011 | Burbank et al. | |
| 8,261,385 B2 | 9/2012 | Mazzei et al. | |
| 8,269,825 B1 | 9/2012 | Vu et al. | |
| 8,302,213 B2 | 11/2012 | Kriesel | |
| 8,359,689 B2 | 1/2013 | Warren et al. | |
| 8,399,085 B2 | 3/2013 | Moore, III et al. | |
| 8,464,720 B2 | 6/2013 | Pigazzi et al. | |
| 8,511,314 B2 | 8/2013 | Pigazzi et al. | |
| 8,648,900 B2 | 2/2014 | Vu et al. | |
| 2008/0283063 A1 * | 11/2008 | Wilcox | A42B 3/28 128/206.17 |
| 2010/0307509 A1 | 12/2010 | King et al. | |
| 2011/0253150 A1 | 10/2011 | King et al. | |
| 2012/0054966 A1 * | 3/2012 | Bacon | A47G 9/1081 5/636 |
| 2012/0297526 A1 * | 11/2012 | Leon | A42B 3/08 2/413 |

* cited by examiner

A-A
END VIEW

SIDE VIEW

PATIENT PROTECTION SYSTEM CONFIGURED TO PROTECT THE HEAD OF A PATIENT

CROSS REFERENCE TO RELATED APPLICATIONS

The present patent application claims the benefit of the filing dates of U.S. Provisional Patent Application No. 62/113,825, filed on Feb. 9, 2015, and U.S. Provisional Patent Application No. 62/156,583, filed on May 4, 2015, the disclosures of which are hereby incorporated by reference in their entirety. The present patent application is also a continuation-in-part of U.S. patent application Ser. No. 14/205,520, filed on Mar. 12, 2014, which claims priority to U.S. Provisional Patent Application No. 61/793,874, filed on Mar. 15, 2013, the disclosures of which are also hereby incorporated by reference in their entirety.

BACKGROUND OF THE INVENTION

1. Field of the Invention

The present application relates to a patient protection system comprising a head mask structure, configured to protect the head of a patient, for use in robotic surgical procedures.

2. Description of Related Art

Robotic operation equipment may be programmed to take a shortest path between a point where an operating instrument is to a point where the operating instrument is desired to be. A surgeon may make a mistake in moving an operating instrument from a point where the operating instrument currently is, to a point where the operating instrument is desired to be. A problem exists wherein one or more arms of a robotic operation device may strike a patient, damaging the patient's face or eye. To restrict or minimize the possibility of a patient being injured due to these errors or mistakes made by robotic operation equipment or a surgeon during robotic surgery, a need exists for a protective face mask configured to cover the face or face area of a patient.

SUMMARY OF THE INVENTION

An embodiment of the invention described in the present patent application may relate to a patient protection system configured for protecting a patient's face and eyes during a surgical procedure, the system comprising: a face mask structure comprising a foam body having an exterior surface and an interior surface configured to be oriented towards the patient's face to cover the patient's face during the surgical procedure; and at least one foam pad positioned on the interior surface of the face mask structure and configured to contact the patient's face during the surgical procedure, wherein the face mask structure and the foam pad are manufactured from different types of foam.

An embodiment of the invention described in the present patent application may relate to a patient protection system, wherein the face mask structure is manufactured from a first type of foam and the at least one foam pad is manufactured from a viscoelastic foam that is softer than the first type of foam.

An embodiment of the invention described in the present patent application may relate to a patient protection system, wherein the at least one foam pad includes at least one first foam pad positioned on the interior surface of the face mask structure to come into contact with a chin of the patient and at least one second foam pad positioned on the interior surface of the face mask structure to come into contact with a forehead of the patient.

An embodiment of the invention described in the present patent application may relate to a patient protection system, wherein the face mask structure further comprises: an eye opening configured to allow observation of the patient's eyes during the surgical procedure.

An embodiment of the invention described in the present patent application may relate to a patient protection system, wherein the face mask structure further comprises one or more side notches formed therein and configured to allow intubation of the patient during robotic surgery.

An embodiment of the invention described in the present patent application may relate to a patient protection system wherein the face mask structure further comprises an intubation observation opening formed on the exterior surface thereof and extending through the interior surface and configured to allow observation of an intubation of the patient during the surgical procedure.

An embodiment of the invention described in the present patent application may relate to a patient protection system further comprising a strap operatively connected to the face mask structure and configured to secure the face mask structure to the patient during the surgical procedure.

An embodiment of the invention described in the present patent application may relate to a patient protection system further comprising one or more plate members affixed to the exterior surface of the face mask structure.

An embodiment of the invention described in the present patent application may relate to a patient protection system further comprising a head rest unit configured to contact and support a head of the patient during the surgical procedure, wherein the head rest unit is comprised of a foam material.

An embodiment of the invention described in the present patent application may relate to a patient protection system, wherein the head rest further comprises one or more strap receiving members formed on an exterior surface thereof; wherein the one or more strap receiving members are configured to coact with one or more straps of the face mask structure to secure the face mask structure during robotic surgery.

An embodiment of the invention described in the present patent application may relate to a face mask for use during a surgical procedure, comprising: a foam body comprising an exterior surface and an interior surface configured to cover a face of the patient during the surgical procedure; a chin area channel extending from the exterior surface to the interior surface of the foam body at a bottom area of the foam body and configured to allow intubation of the patient during surgical procedure; and fastener provided on the exterior surface of the foam body in the bottom area of the foam body and configured to allow opening and closure of the chin area channel during the surgical procedure.

An embodiment of the invention described in the present patent application may relate to a face mask, further comprising an eye opening formed in the exterior surface of the foam body and configured to allow observation of the patient's eyes during robotic surgery.

An embodiment of the invention described in the present patent application may relate to a face mask further comprising: an eye shield positioned over the eye opening and configured to cover a patient's eyes and to allow observation of a patient's eyes during the surgical procedure; and one or more fasteners configured to removably attach the eye shield to the foam body over the eye opening.

An embodiment of the invention described in the present patent application may relate to a face mask further comprising: one or more plate members positioned on the exterior surface of the foam body and configured to protect the patient during the surgical procedure.

An embodiment of the invention described in the present patent application may relate to a face mask, wherein the one or more plate members comprise: one or more protection plates positioned on the foam body to protect a forehead of a patient and a side of the patient's face; and one or more chin protection plates positioned on the foam body to protect a chin of the patient.

An embodiment of the invention described in the present patent application may relate to a face mask, wherein at least one foam pad is positioned on the interior surface of the face mask structure and configured to contact the patient's face during the surgical procedure.

An embodiment of the invention described in the present patent application may relate to a method for protecting a face of a patient during surgical procedure comprising: placing a patient's head on a head rest unit configured to support the patient's head; placing a face mask structure configured to protect the patient's face over the patient's face, the face mask structure comprising: a foam body having an exterior surface and an interior surface configured to be oriented towards the patient's face to cover the patient's face during the surgical procedure; at least one foam pad positioned on the interior surface of the face mask structure and configured to contact the patient's face during the surgical procedure; and securing the face mask structure to the head rest unit.

An embodiment of the invention described in the present patent application may relate to a method, wherein the face mask structure is manufactured from a first type of foam and the at least one foam pad is manufactured from a viscoelastic foam that is softer than the first type of foam.

An embodiment of the invention described in the present patent application may relate to a method, wherein the face mask structure further comprises a chin area channel extending from the exterior surface to the interior surface of the foam body at a bottom area of the foam body; and the method further comprises intubating the patient and positioning an intubation tube within the chin area channel.

An embodiment of the invention described in the present patent application may relate to a method, wherein the face mask structure further comprises an eye shield positioned over an eye opening formed in the foam body, the eye shield configured to cover a patient's eyes and to allow observation of a patient's eyes during the surgical procedure; and one or more attachment mechanisms configured to removably attach the eye shield to the foam body; and the method further comprises closing an removably securing the eye shield in place.

One feature or aspect of an embodiment of the present invention is a method of protecting a patient on a medical procedure table during a robotic operation, said method comprising use of a robotic patient protection system comprising a head mask structure configured to protect the head of a patient for use in robotic surgical procedures, said mask structure comprising: a face covering polyethylene foam body configured to substantially conform to the face of the patient; said face covering polyethylene body being covered by a hard plastic covering membrane, configured to be disposed away from the face of the patient, covering the outer surface of said polyethylene foam body; a viscoelastic open cell foam disposed on the inner portion of said body which is configured to be disposed toward the patient's face; a headrest member configured to hold the back of the head of the patient during an operation which headrest member comprises a hollowed out portion configured to receive the back of the head of the patient; a strap member attaching arrangement with a hook or loop strap connected to said hard portion of said outer surface of said mask; a hook or loop member connected to said headrest member and configured to attach to said strap member hook or loop attaching arrangement; said face covering polyethylene body covered with said hard plastic covering providing a safety covering for the head of the patient in the event of a malfunction by either the surgeon or the software thereby preventing or substantially preventing or minimizing injury to the patient upon a portion of the robotic surgical apparatus striking the hard plastic covered body; putting the back of the head of the patient in the headrest; placing said face covering polyethylene foam body with the hard covering and the viscoelastic layer on the patient and connecting the straps to the headrest; and preventing or substantially preventing or minimizing injury to the patient upon a portion of the robotic surgical apparatus striking the hard plastic cover body.

Another feature or aspect of an embodiment is believed at the time of the filing of this patent application to possibly reside broadly in a method of protecting a patient on a medical procedure table during a robotic operation, said method comprising use of a head mask structure configured to protect the head of a patient, said mask structure comprising: a face covering foam body configured to substantially conform to the face of the patient; said face covering body being covered by a hard plastic covering configured to be disposed away from the face of the patient covering the outer surface of said foam body; a soft face-conforming material disposed on the inner portion of said face covering body which soft face-conforming material is disposed and configured to be disposed toward the patient's face; a headrest member configured to hold the back of the head of the patient during an operation which headrest member comprises a hollowed out portion configured to receive the back of the head of the patient; strap member attaching arrangement connected to one of: said hard portion of said outer surface of said mask; and said headrest member; a connecting member connected to said headrest member and configured to attach to said strap member hook or loop attaching arrangement; said face covering body covered with said hard plastic covering providing a safety covering for the head of the patient in the event of a malfunction by either the surgeon or the software thereby said safety covering preventing or substantially preventing or minimizing injury to the patient upon a portion of the robotic surgical apparatus striking the hard plastic covering said face covering body; said method comprising the steps of: putting a portion of the head of the patient in the headrest; placing said face covering foam body with the hard covering on the patient and connecting the attachment arrangement to the headrest; and preventing or substantially preventing or minimizing injury to the patient upon a portion of the robotic surgical apparatus striking the hard plastic cover body.

Yet another feature or aspect of an embodiment is believed at the time of the filing of this patent application to possibly reside broadly in a method of protecting a patient on a medical procedure table during a robotic operation, said method comprising use of a head mask structure configured to protect the head of a patient, said mask structure comprising: a first head covering body part configured to substantially conform to the face of the patient; said first head covering body part being covered by a hard plastic covering configured to be disposed away from the face of the patient covering the outer surface of said first head covering body part; a soft face conforming material disposed on the inner portion of said first head covering body part which soft face-conforming material is disposed and configured to be disposed toward the patient's face; a second head covering body part configured to hold the back of the head of the patient during an operation which second head covering body part comprises a hollowed out portion configured to receive the back of the head of the patient; a part attaching arrangement connected to one of: said hard portion of said first head covering body part; and said second head covering body part; a connecting member connected to said second head covering body part and configured to attach to said part attaching arrangement; said first head covering body part covered with said hard plastic covering providing a safety covering for the head of the patient in the event of a malfunction by either the surgeon or the software thereby said safety covering preventing or substantially preventing or minimizing injury to the patient upon a portion of the robotic surgical apparatus striking the hard plastic covering said first head covering body part; said method comprising the steps of: putting a portion of the head of a patient in said first head covering body part; putting a portion of the head of the patient in said second head covering body part; aligning said first head covering body part with the hard covering on the patient and connecting the part attachment arrangement to said second head covering body part; and preventing or substantially preventing or minimizing injury to the patient upon a portion of the robotic surgical apparatus striking the hard plastic cover body.

Still another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said mask structure further comprises: said first connecting member attaching arrangement is configured to be connected to said first head covering body part; and said second connecting member attaching arrangement is configured to be connected to said second head covering body part.

A further feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said mask structure further comprises a head-conforming material disposed on at least one of: the inner portion of said first head covering body part and said second head covering body part which is configured to be disposed toward the patient's face and configured to be substantially matchable to the patient's face.

Another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said head-conforming material is sufficiently soft to conform to the patient's head and is configured to be disposed toward the patient's head and configured to be substantially matchable to the patient's head.

Yet another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said head-conforming material comprises a viscoelastic material being sufficiently soft to conform to the patient's face and is configured to be disposed toward the patient's head and configured to be substantially matchable to the patient's head.

Still another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said viscoelastic material comprises an open cell foam.

A further feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said second head covering body part is configured to hold the back of the head of the patient during a medical procedure, which second head covering body part comprises a hollowed out portion configured to receive the back of the head of the patient.

Another feature or aspect of an embodiment is believed at the time of the filing of this patent application to possibly reside broadly in the method of protecting a patient on a medical procedure table during a robotic operation, said method comprising use of a head mask structure configured to protect the head of a patient, wherein said first connecting member attaching arrangement comprises a strap, which strap comprises a hook or loop arrangement configured to be connected to said hard covering of said head mask structure.

Yet another feature or aspect of an embodiment is believed at the time of the filing of this patent application to possibly reside broadly in a head protecting mask configured to protect a patient on a medical procedure table during a robotic medical procedure, which head protecting mask is configured for use according to the method, said head protecting mask comprising: a head covering body comprising a first part and a second part, said first head covering body part comprising a hollowed out portion configured to receive a portion configured to receive a portion of the head of a patient; said first head covering body part being configured to be disposed above said second head covering body part during use and being covered by a hard covering, configured to be disposed away from the head of the patient, covering the outer surface of said first head covering body part; said second head covering body part being configured to hold a portion of the head of the patient during a medical procedure, which second head covering body part comprises a hollowed out portion configured to receive a portion of the head of the patient; a first connecting member attaching arrangement connected to one of: said first head covering body part; and said second head covering body part; a second connecting member attachment arrangement connected to the other of: said first head covering body part; and said second head covering body part; said first head covering body part covered with said hard covering being configured to be disposed to provide a safety covering for the head of the patient in the event of a malfunction, such as, by either the surgeon or the software, wherein said hard covering is configured to prevent or substantially prevent or minimize injury to the patient upon a portion of the robotic surgical apparatus striking the hard covering of said head covering body.

Still another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein: said first connecting member attaching arrangement is configured to be connected to said first head covering body part; and said second connecting member attaching arrangement is configured to be connected to said second head covering body part.

A further feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head protecting mask further comprises a head-conforming material disposed on at least one of: the inner portion of said first head covering body part and said second head covering body part which is configured to be disposed toward the patient's head and configured to be substantially matchable to the patient's head.

One feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head protecting mask further comprises a head-conforming material disposed on at least one of: the inner portion of said first head covering body part and said second head covering body part which is configured to be disposed toward the patient's face and configured to be substantially matchable to the patient's face.

Another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head-conforming material is sufficiently soft to conform to the patient's head and is configured to be disposed toward the patient's head and configured to be substantially matchable to the patient's head.

Yet another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said head-conforming material comprises a viscoelastic material being sufficiently soft to conform to the patient's face and is configured to be disposed toward the patient's head and configured to be substantially matchable to the patient's head.

Still another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said viscoelastic material comprises an open cell foam.

A further feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said second head covering body part is configured to hold the back of the head of the patient during a medical procedure, which second head covering body part comprises a hollowed out portion configured to receive the back of the head of the patient.

Another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said first connecting member attaching arrangement comprises a strap, which strap comprises a hook or loop arrangement configured to be connected to said hard covering of said head protecting mask.

Yet another feature or aspect of an embodiment is believed at the time of the filing of this patent application to possibly reside broadly in the head protecting mask configured to protect a patient on a medical procedure table during a robotic medical procedure, which head protecting mask is configured for use according to the method, wherein said second connecting member attachment arrangement connected to said second head covering body part.

BRIEF DESCRIPTION OF THE DRAWING(S)

Figure 19:
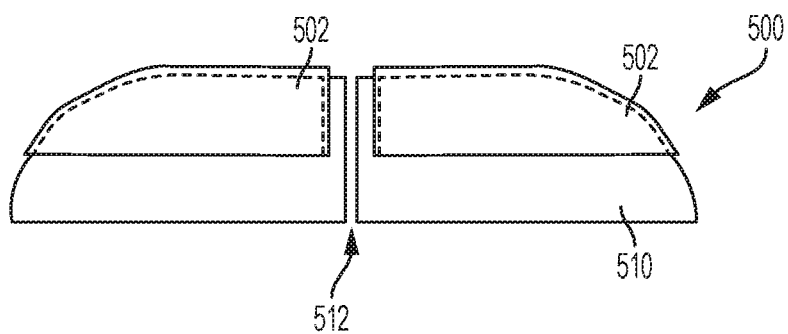
Figure 20:
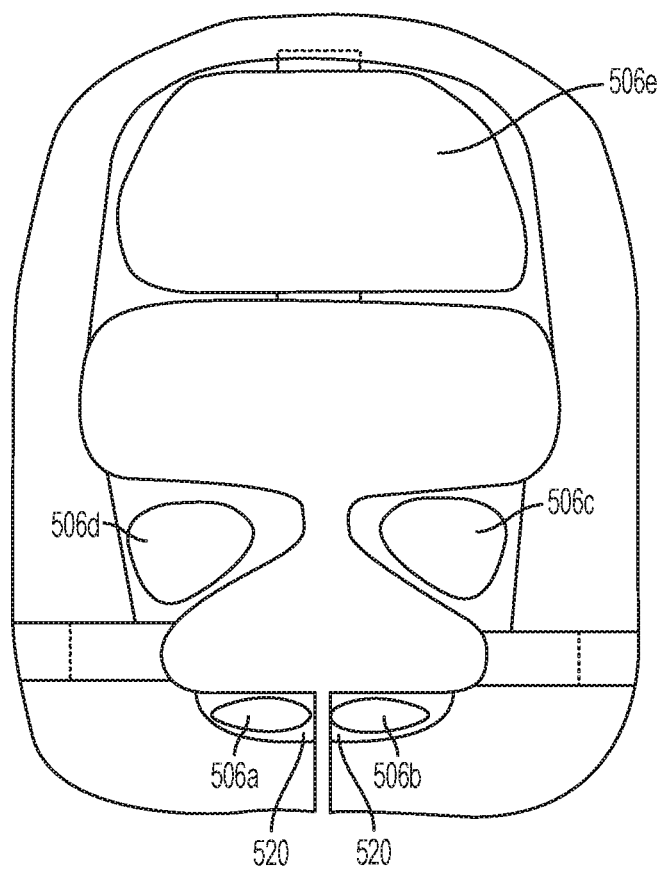
Figure 22:
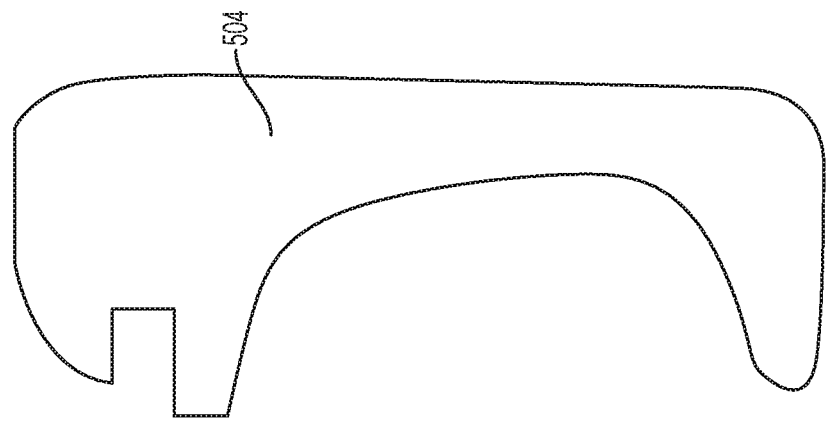
Figure 21:
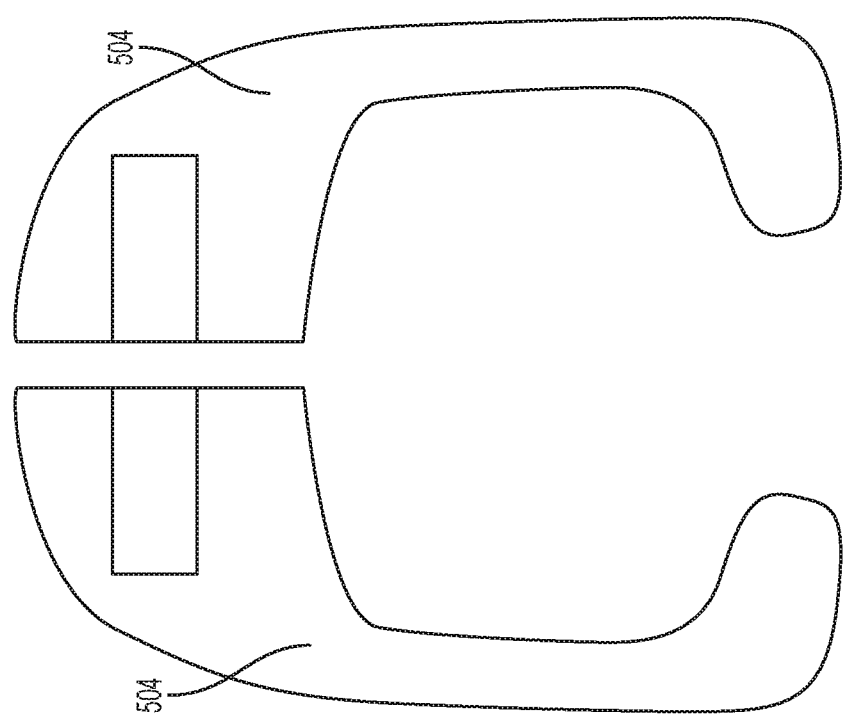
Figure 23:
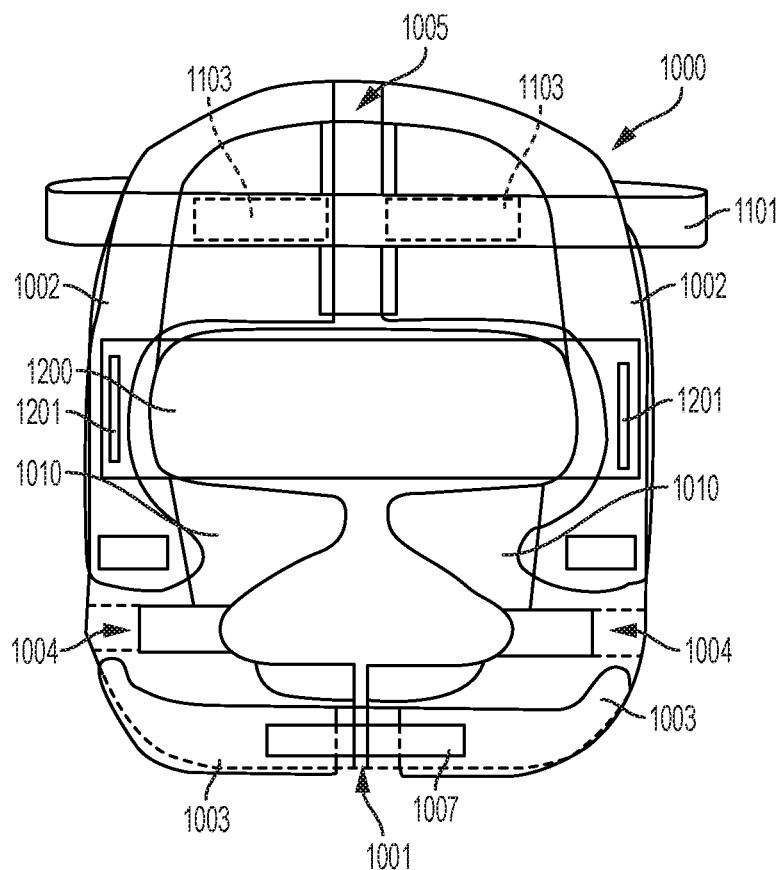
Figure 24:
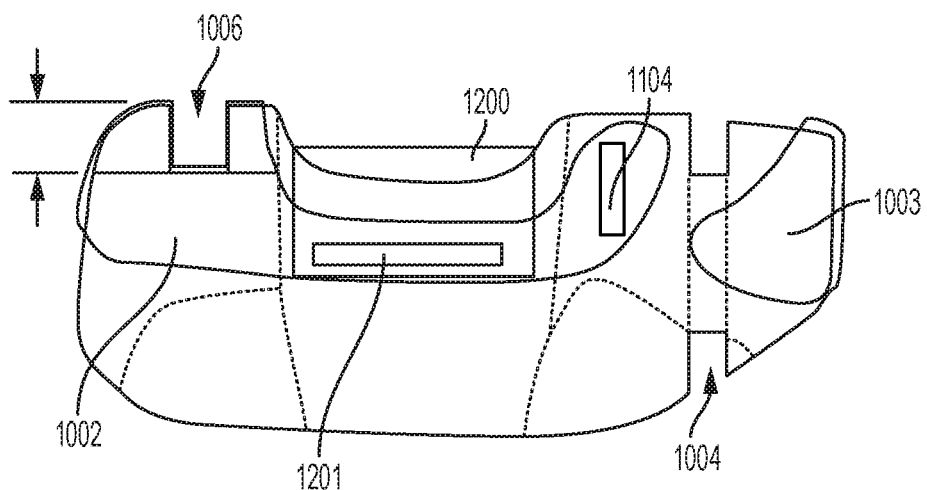
Figure 25:
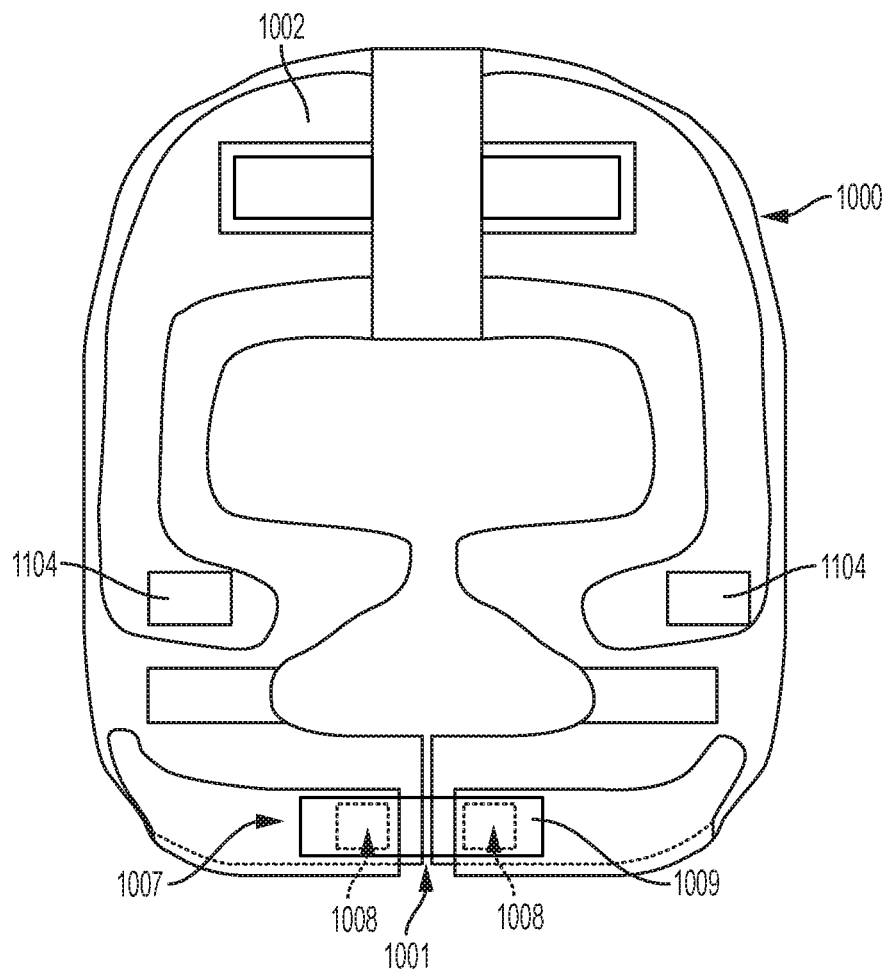
Figure 26:
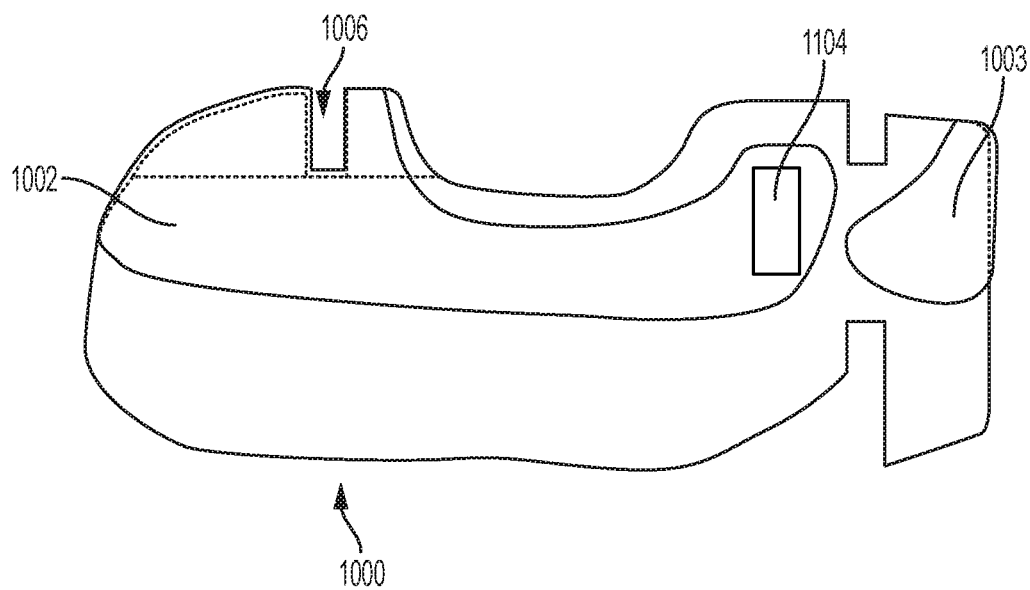
Figure 27:
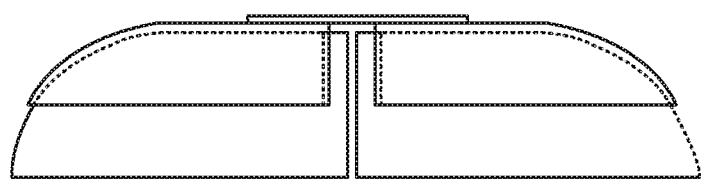
Figure 28:
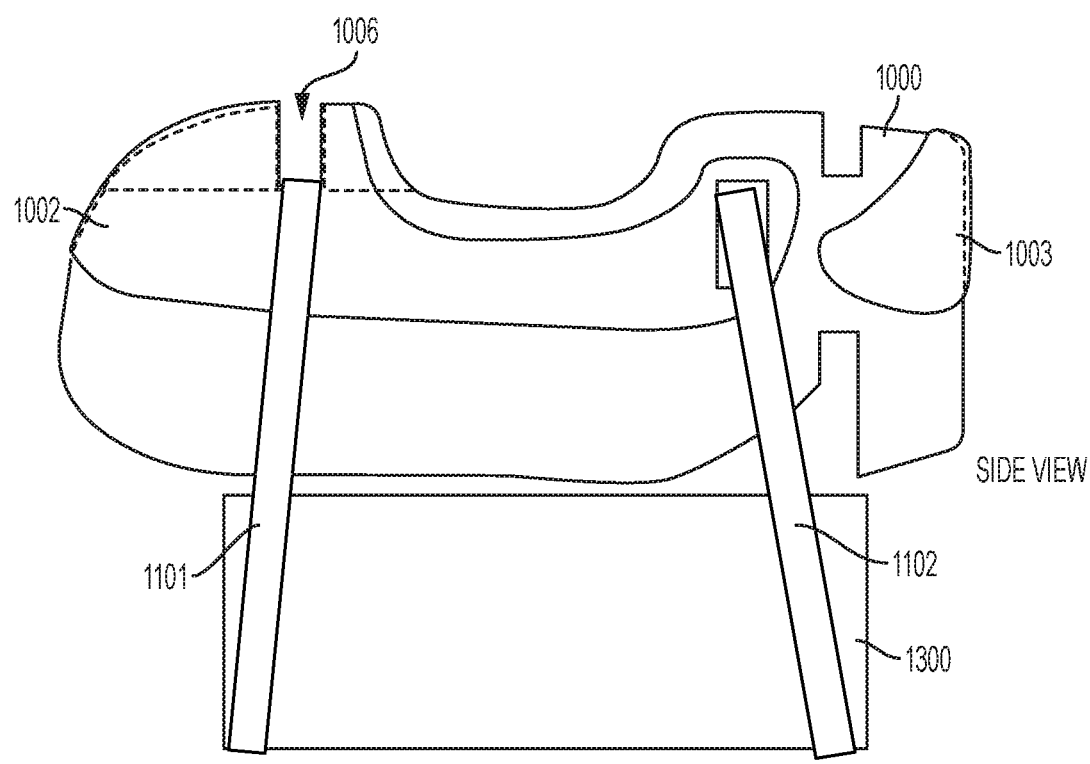
Figure 29:
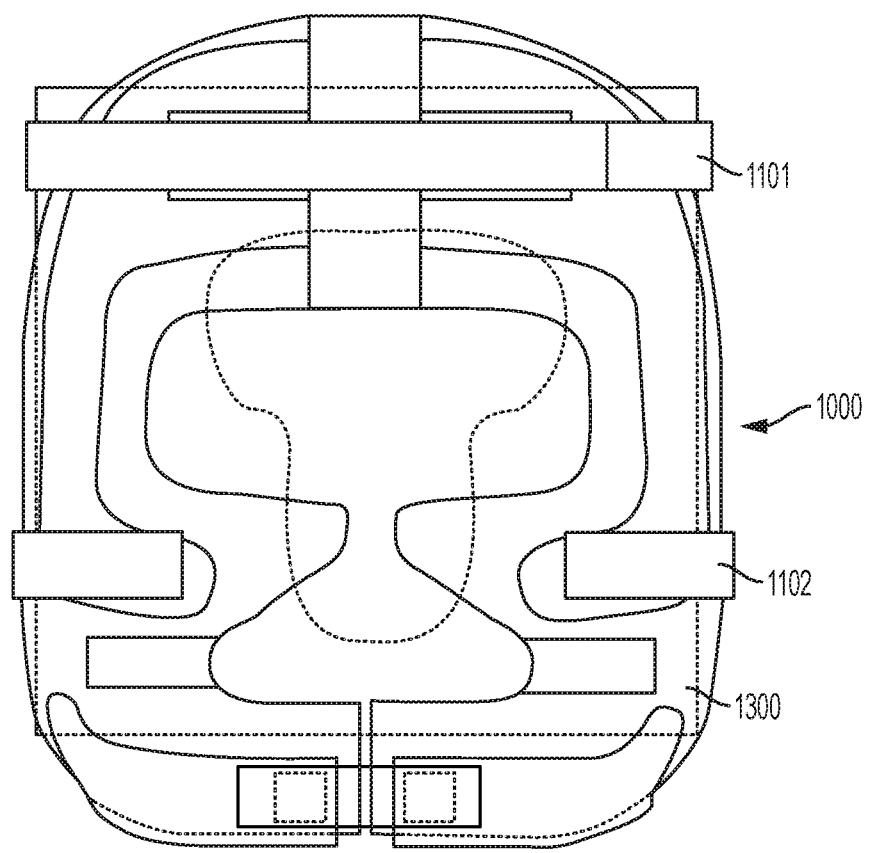

In FIG. 19 the mask is shown from the bottom side with protection plates affixed;

FIG. 20 shows a reverse view of an embodiment of a mask wherein foam relief pads are positioned within the inside of the mask;

FIG. 21 shows a front view of an embodiment of embedded protection plates not embedded without a mask;

FIG. 22 shows a side view of an embodiment of embedded protection plates not embedded into a mask;

FIG. 23 shows a front view of an embodiment of the mask, wherein the protection plates are disposed on the surface of the mask;

FIG. 24 is a side view of an embodiment of the mask, wherein the plastic protection plates are disposed on the surface of the mask;

FIG. 24 shows greater detail of an embodiment of an eye shield, and means for attaching thereof, shown in FIGS. 23 and 24;

FIG. 25 shows a top view of an embodiment of the mask;

FIG. 26 shows a side view, of an embodiment of the mask;

FIG. 27 shows an end view of an embodiment of the mask;

FIG. 28 shows a side view of an embodiment of the mask secured to a head rest by means of straps; and FIG. 29 shows a top view of the embodiment shown in FIG. 28.

DESCRIPTION OF THE INVENTION

Figure 1:
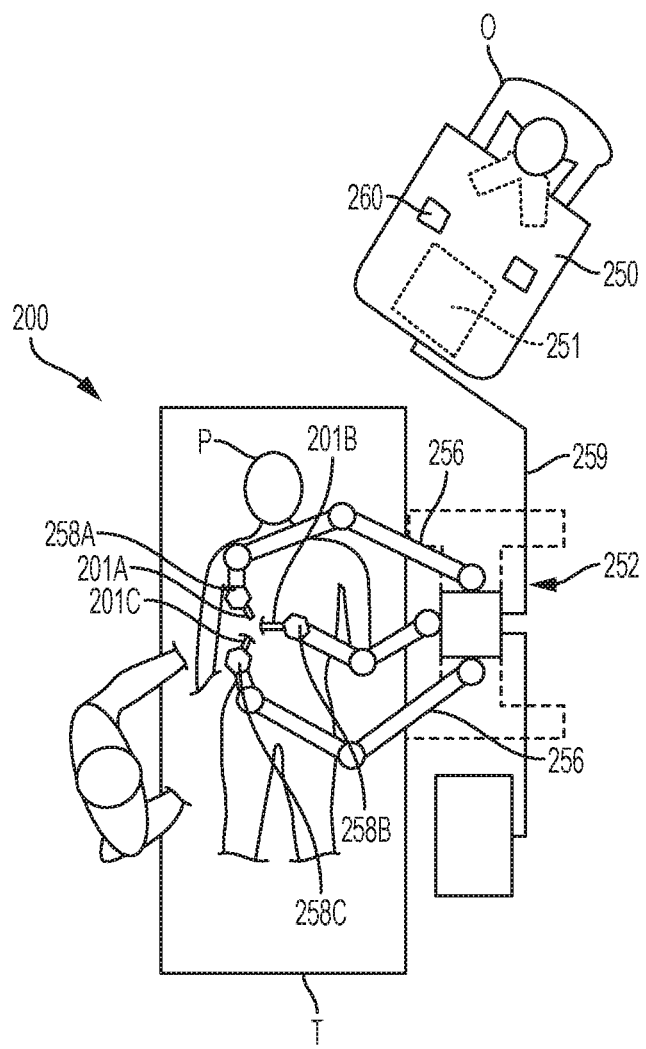
FIG. 1 is a block diagram of an embodiment of a robotic surgery system to perform minimally invasive robotic surgical procedures using one or more robotic surgical arms with a strap drive train.

FIG. 1 shows a block diagram of an example of a robotic surgery system 200 configured to perform minimally invasive robotic surgical procedures using one or more robotic arms with a strap drive. Robotic surgery generally involves the use of a robot manipulator that has multiple robotic manipulator arms. One or more of the robotic manipulator arms often supports a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 258B) is used to support a stereo or three dimensional surgical image capture device 210 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

With continued reference to FIG. 1, a user or operator O (generally a surgeon) performs a minimally invasive surgical procedure on patient P, positioned on table T, by manipulating control input devices 260 at a master control console 250. A computer 251 of the console 250 directs movement of robotically controlled endoscopic surgical instruments 201A-201C by means of one or more control cables 259, effecting movement of the instruments using a robotic patient-side system 252 (also referred to as a patient-side cart). The robotic patient-side system 252 has one or more robotic arms 258A, 258B, and 258C. In one possible embodiment of the Da Vinci Surgical System, the one or more robotic arms 258A, 258B, and 258C have a strap drive system. Typically, the robotic patient-side system 252 includes at least three robotic manipulator arms 258A-258C supported by linkages 256, with a central robotic arm 258B supporting an endoscopic camera 201B and the robotic arms 258A, 258C to left and right of center supporting surgical instruments 201A and 201C.

Further referencing FIG. 1, robotic patient-side system 252 generally includes a positioning portion and a driven portion. The positioning portion of the robotic patient-side system 252 remains in a fixed configuration during surgery while manipulating tissue. The driven portion of the robotic patient-side system 252 is actively articulated under the direction of the operator O generating control signals at the surgeon's console 250 during surgery. The actively driven portion of the robotic patient-side system 252 is generally referred to herein as the robotic arms, or alternatively, robotic surgical manipulators.

It is understood in the art that a risk exists that the one or more robotic arms 258A-258C may strike the face of a patient during a surgical procedure. This increases the risk of injury to a patient's face or eye. Thus, a need exists to protect a patients' face during a surgical procedure involving a robotic surgery system 200.

Figure 2:
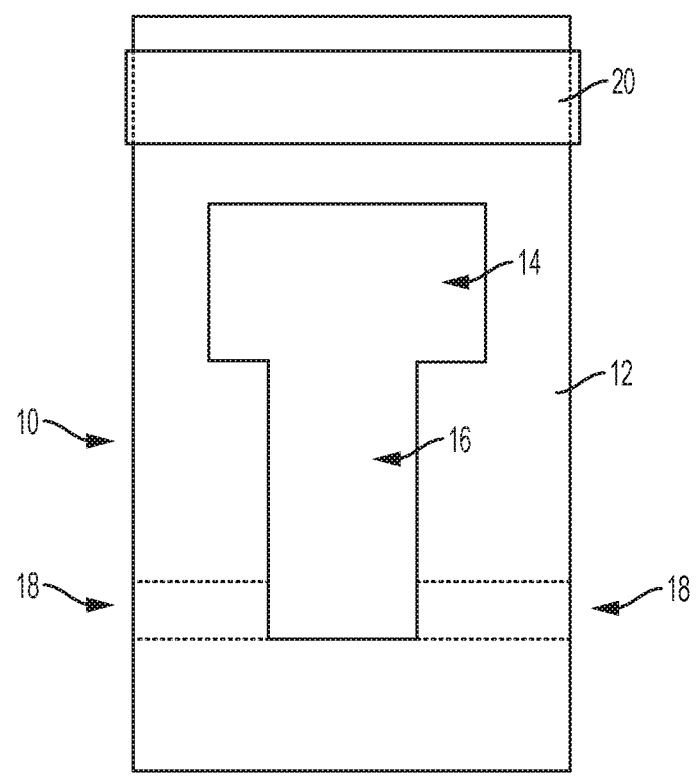
FIG. 2 shows a top view of one possible embodiment of a face unit of a patient protection system according to one possible embodiment of the present application.

As shown in FIG. 2, in an embodiment, face mask 10 may comprise a body made from plastic foam material or polyurethane foam material, which can possibly be deformed upon impact by an operating instrument. The body 12 of the face mask 10 may also be somewhat deformed by the face of a patient to form a reasonably comfortable fit between the face of the patient and the face mask 10. In an embodiment, the face mask 10 may comprise a plastic plate protecting layer, made from hard plastic, which may protect the body 12 of the mask 10 and a patient from moderate to severe impact with an operating instrument or other parts of the movable arms of the robotic operating system. The body 12 of the mask 10 may be made of, for example, a polyethylene foam or alternatively of a polypropylene foam. In order for operating room personnel to be able to observe the eyes of a patient during an operation, an opening 14 is provided in the body 12 of the mask 10. Further, in order for operating room personnel to be able to observe the intubation in the mouth of a patient during an operation an opening 16 is provided in the body 12 of the mask 10. As shown in FIG. 2, the opening 16 extends from the opening 14. One or more side notch 18 may be included and configured to allow operating room staff to intubate a patient, shown in dotted lines in FIG. 2. One or more straps 20 may be configured to hold the face mask 10 to a patient may be provided.

Figure 3:
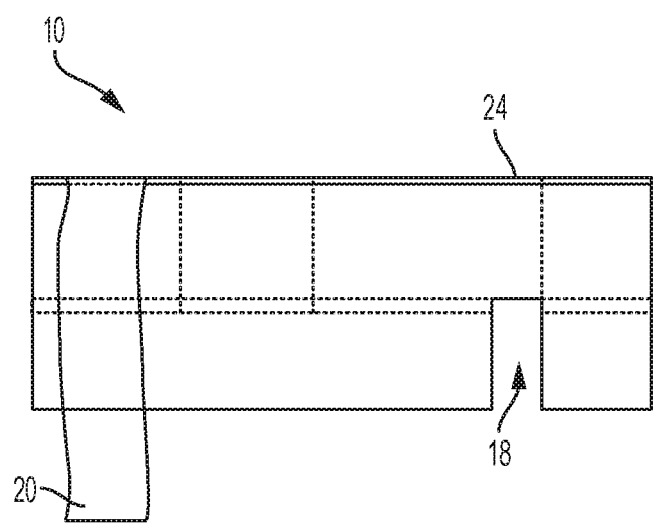
FIG. 3 shows a side view of the face unit of the possible embodiment of a patient protection system as shown in FIG. 2.

FIG. 3 depicts an embodiment including side notch 18, which permits intubation equipment to pass through the mask 10. One or more strap 20 is connected to the mask 10 in order to hold the mask 10 in place on a patient. In an embodiment, a protecting layer 24, which may protect the body 12 of the mask 10 from moderate or severe impact with an operating instrument or other parts of the movable arms of the robotic operating system, is also shown in FIG. 3. In an embodiment, protecting layer 24 may be made from hard plastic. Alternatively, metal such as aluminum or another material such as a ceramic, could be used in an embodiment of protecting layer 24.

Figure 4:
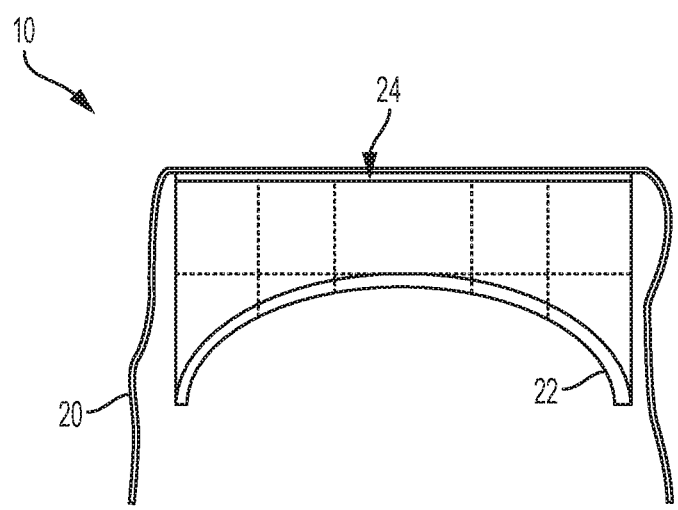
FIG. 4 shows an end view of the face unit of the possible embodiment of a patient protection system as shown in FIG. 2.

As shown in FIG. 4, in an embodiment a layer of viscoelastic foam 22 may be attached to the body 12 of the mask 10 and configured to contact the face of a patient during use. The viscoelastic foam layer 22 may generally conform to the face of a patient in order to distribute the load of the mask 10 over the face of a patient in a relatively comfortable manner. An embodiment of protecting layer 24 is also shown.

In embodiments, protecting layer 24 may be made from a number of hard plastic materials, such as those used for hockey masks, such as, for example, fiberglass, Kevlar, thermoplastic composites, or thermoset composites.

In the possible embodiment, the body 12 of the mask 10 may be about twelve inches long and about ten inches wide. Opening 14 may be about two and a half inches long and about five and a half inches wide. Opening 16 may be about three and a half inches long and about three inches wide. The one or more side notch 18 for an intubation tube may be about one inch long and span the width of the face mask 10. In an embodiment, opening 16 may be disposed about two inches from the bottom side of the face mask 10. An embodiment of opening 14 may be disposed about four inches from the top side of the face mask 10. Measurements of other possible embodiments may be greater or lesser than the values disclosed above.

Figure 5:
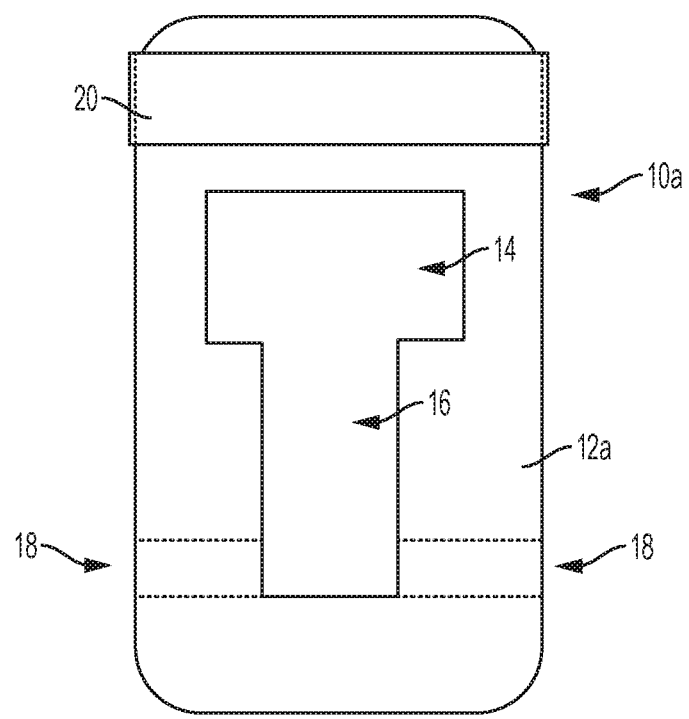
FIG. 5 shows a top view of another possible embodiment of a face unit of a patient protection system according to one possible embodiment of the present application.

FIG. 5 shows a front view of an embodiment of a face mask 10a in which the corners of the face mask 10a are curved. The face mask 10a comprises a body 12a which is rounded at the corners, and may be comprised of a foam. The face mask 10a also comprises the opening 14, the opening 16, one or more side notch 18 for an intubation tube, and a strap 20.

Figure 6:
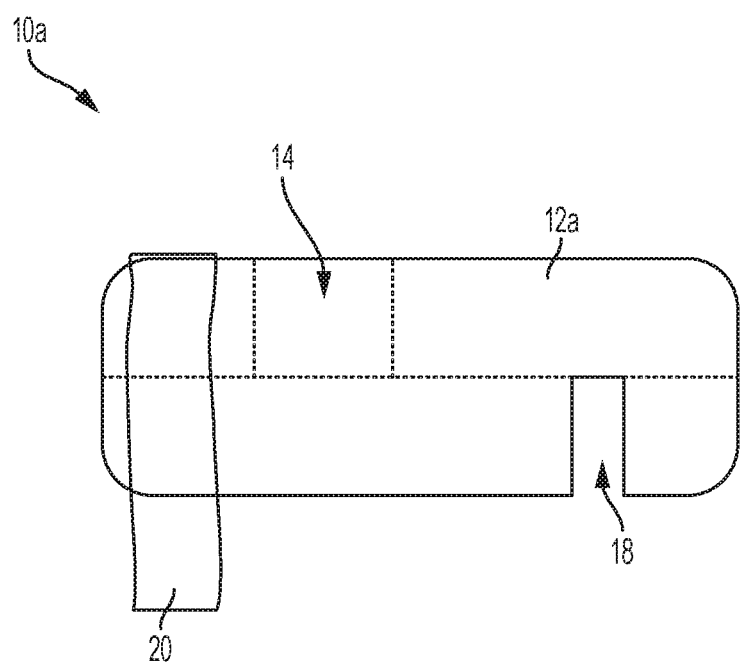
FIG. 6 shows a side view of the face unit of the possible embodiment of a patient protection system as shown in FIG. 5.

FIG. 6 shows a side view of an embodiment of the face mask 10a of FIG. 5. The face mask 10a comprises a body 12a, opening 14 for viewing a patient's eyes, one or more side notch 18 for an intubation tube, and strap 20. In yet another embodiment of the present application, the strap 20 could be replaced with other means for connecting the face mask 10a to a head rest unit 90 (not shown) such as screws and threaded holes or unthreaded holes or the like such as spring connectors that engage a tang.

In an embodiment, a patient could be lying face down on a medical procedure table. In such a configuration, the back of the patient's head would then be facing upward, and therefore the protecting layer 24 of the mask would be disposed on the portion of the patient protection system facing upward, which would be above the back portion of the patient's head.

In an embodiment, the side of the head could be covered by the part of the patient protection system facing upward.

Figure 7:
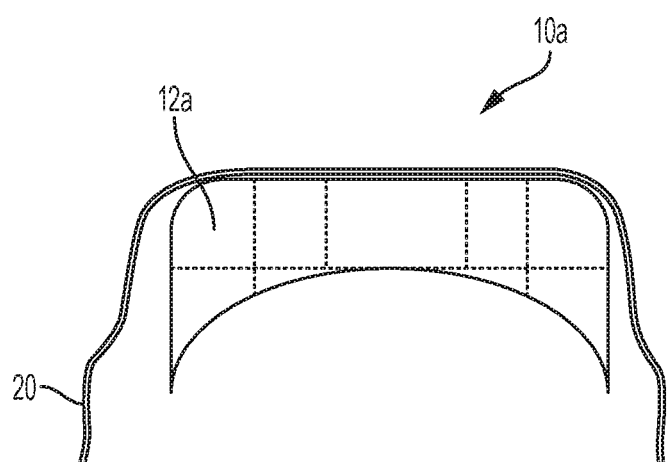
FIG. 7 shows an end view of the face unit of the possible embodiment of a patient protection system as shown in FIG. 5.

FIG. 7 shows an embodiment of face mask 10a of FIGS. 5 and 6 from an end of the mask 10a, but without viscoelastic material on the inside thereof. The mask 10a comprises the body 12a and the strap 20. It should be understood that embodiments of mask 10a may include a viscoelastic foam inner layer 22.

Figure 8:
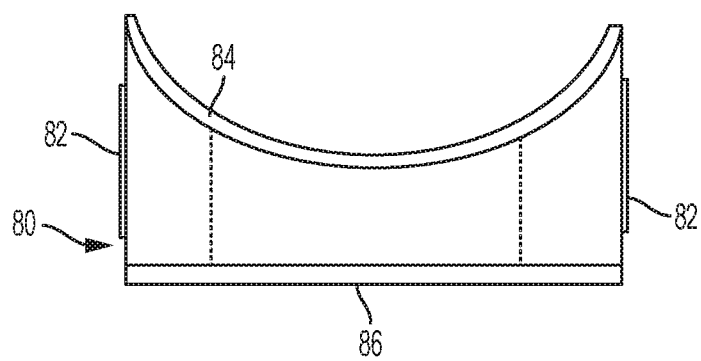
FIG. 8 shows an end view of one possible embodiment of a head rest unit of a patient protection system according to one possible embodiment of the present application.

As shown in FIG. 8, the patient protection system may also comprise a head rest 80 as well as a face mask. One possible embodiment of a head rest 80 is shown in FIG. 8, and may be comprised of a plastic foam material or polyurethane foam material. As shown in FIG. 8, the strap 20 of a face mask of the present application may be connectable to a head rest 80. A hook and loop arrangement 82 is shown on the sides of the head rest 80 to which the straps 20, which also comprise a hook and loop arrangement, can be attached to an embodiment of head rest 80. In at least one possible embodiment of the present application, the head rest 80 may comprise a protecting layer 86 configured to provide additional protection to a patient while in a face-down position. In embodiments, protecting layer 86 may comprise hard plastic. Alternatively, metal such as aluminum or another material such as a ceramic, may be used. Also shown in FIG. 8 is a layer 84 of viscoelastic foam. The layer 84 of the head rest 80 may be configured to contact the back of a patient's head in order to provide a somewhat comfortable head rest for a patient. However, it should be understood that embodiments of head rest 80 may not include a viscoelastic layer 84 and/or protecting layer 86.

Figure 9:
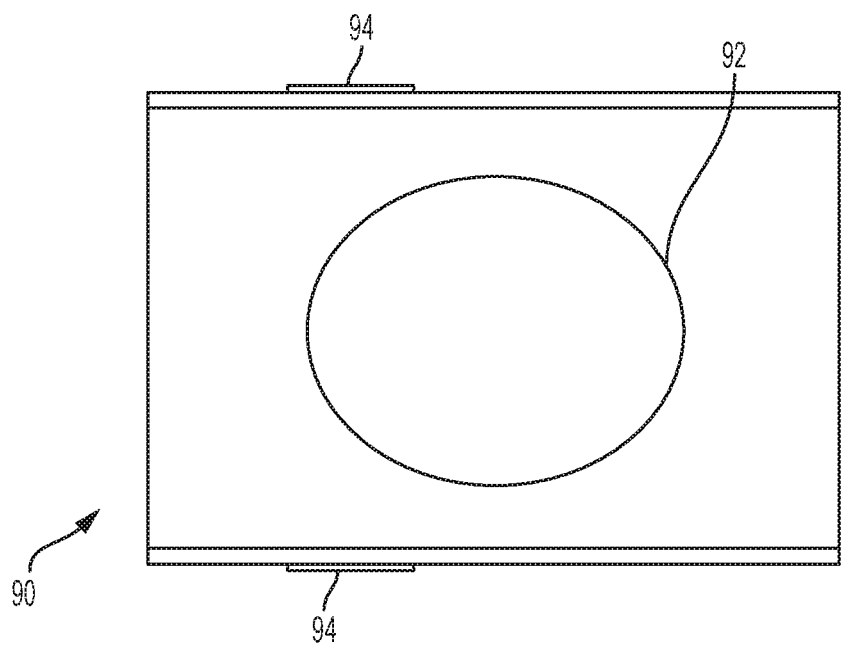
FIG. 9 shows a top view of the head rest unit of the possible embodiment of a patient protection system as shown in FIG. 8.

FIG. 9 shows an embodiment of head rest unit 90 with a hollowed out area 92 into which the back of the head of the patient can be disposed. This hollowed out area 92 is in one embodiment also lined with a viscoelastic material foam which conforms substantially to the head of patient to cradle the back of the head as comfortably as possible. In various embodiments, hollowed out area 92 may extend through head rest unit 90, or a portion thereof. An embodiment may include one or more hook and loop arrangements 94, configured to interact with strap 20. In an embodiment, the head rest unit 90 may not comprise a hole, and may substantially comprise viscoelastic foam.

Figure 10:
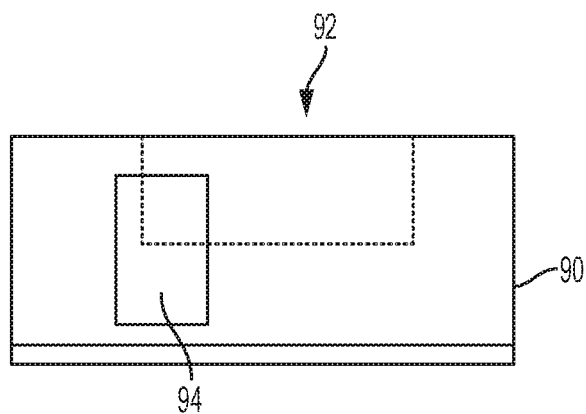
FIG. 10 shows a side view of the head rest unit of the possible embodiment of a patient protection system as shown in FIG. 8.

FIG. 10 shows a side view of an embodiment of head rest unit 90 with a hook and loop arrangement 94 disposed thereon.

Figure 11:
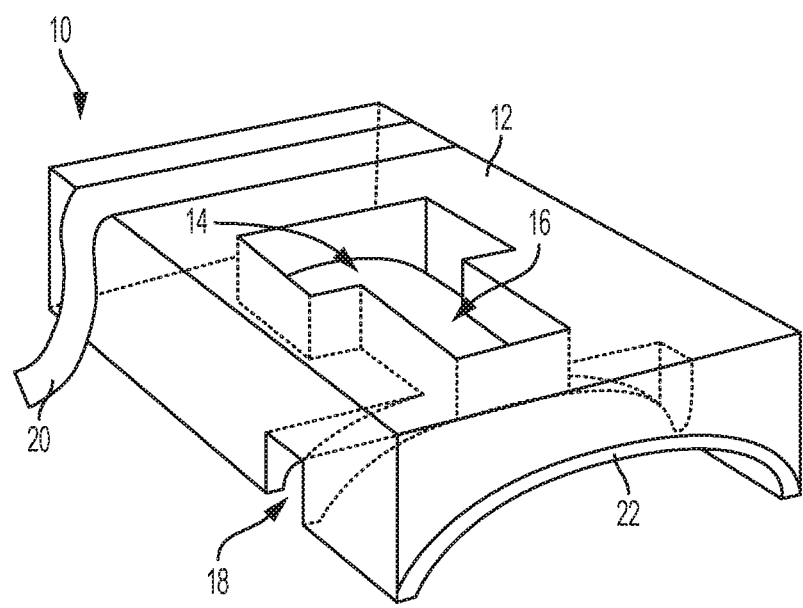
FIG. 11 shows a perspective view of the possible embodiment as shown in FIGS. 2-4.

FIG. 11 is a perspective view of an embodiment of the face mask 10 as shown in FIGS. 2-4. The face mask 10 comprises the body 12, the opening 14 configured to allow observation of a patient's eyes, the opening 16 configured to allow observation of intubation, the one or more side notch 18 configured to receive an intubation tube, the one or more strap 20, and a viscoelastic inner layer 22.

Figure 12:
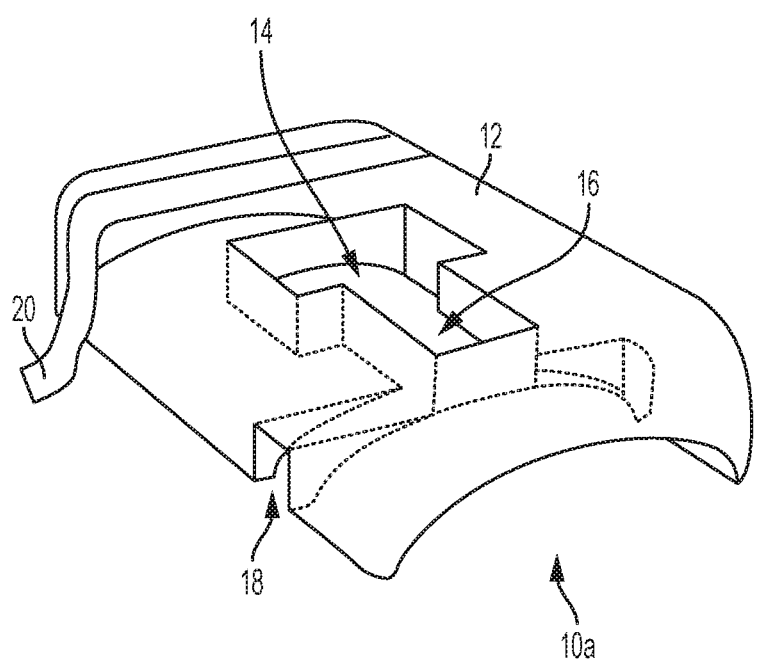
FIG. 12 shows a perspective view of the possible embodiment as shown in FIGS. 5-7.

FIG. 12 is a perspective view of an embodiment of the face mask 10a as shown in FIGS. 5-7. The face mask 10a comprises a body 12a, an opening configured to allow observation of a patient's eyes 14, an opening configured to allow of observation of intubation 16, the one or more side notch 18 configured to receive an intubation tube, and the strap 20.

Figure 13:
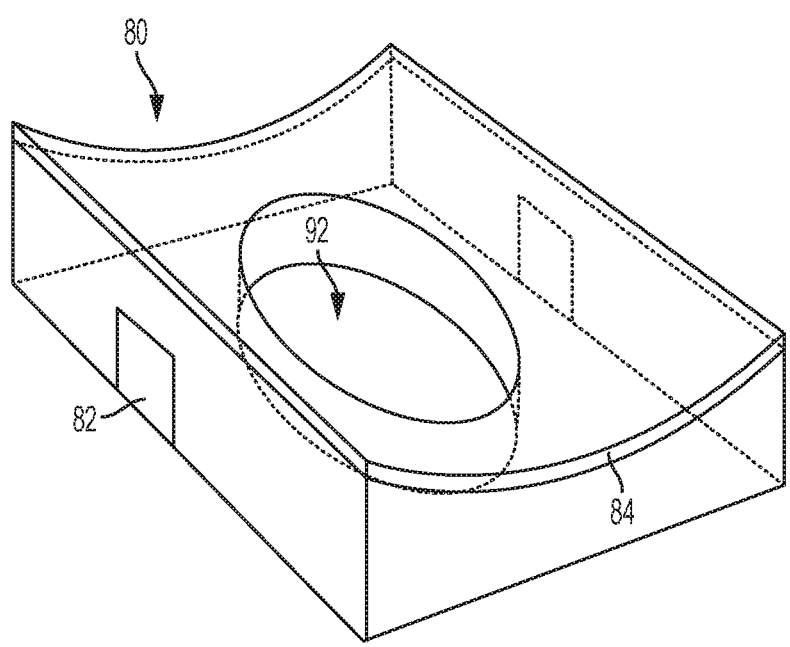
FIG. 13 shows a perspective view of the possible embodiment as shown in FIGS. 8-10.

FIG. 13 is a perspective view of an embodiment of a head rest unit 90. The head rest unit 90 comprises the strap receiving members 82. The strap receiving members 82 may comprise a hook and loop arrangement. In embodiments, the strap receiving members may comprise magnets, snaps, adhesives, or other fixing mechanisms. The head rest unit 90 also may comprise a viscoelastic foam layer 84 and the hollowed out area 92.

Figure 14:
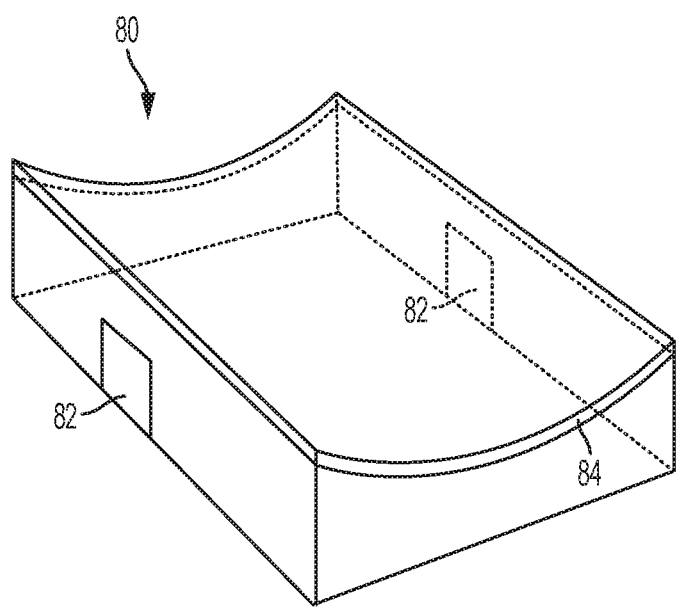
FIG. 14 shows a perspective view of an embodiment of a headrest

FIG. 14 shows a perspective view of an embodiment of a head rest 80 as shown in FIG. 7. The embodiment of head rest 80 does not comprise a hollowed out area. The embodiment of head rest 80 comprises strap receiving members 82 and the viscoelastic foam layer 84.

Figure 15:
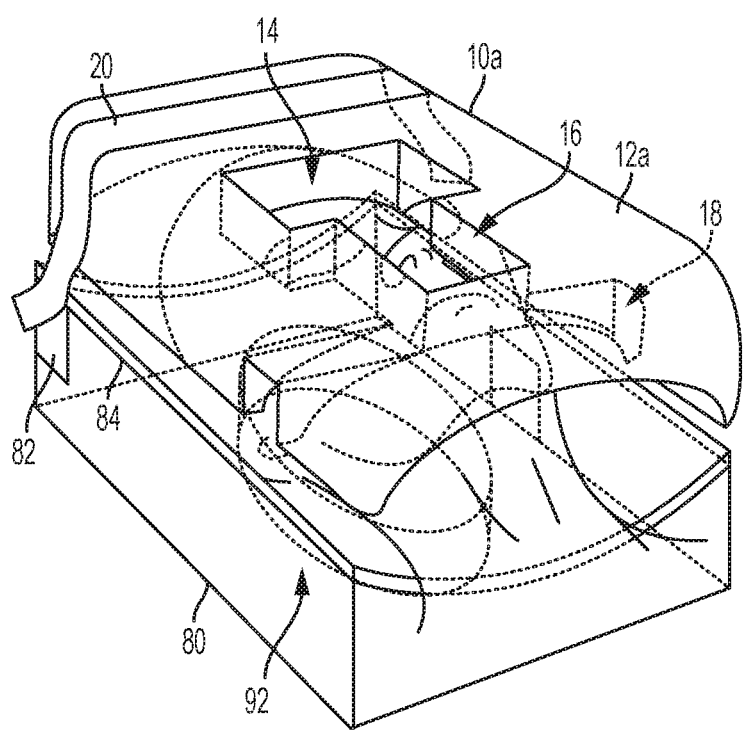
FIG. 15 shows one possible embodiment of the patient protection system of the present application in use with a patient's head disposed in the patient protection system.

FIG. 15 shows an embodiment of the patient protection system in use, comprising the face mask 10a and the head rest 80. FIG. 14 shows the patient protection system for exemplary purposes. In an embodiment, the face mask 10a and the head rest 80 may not touch during use. In another possible embodiment, the face mask 10a and the head rest 80 may touch during use. The face mask 10a comprises the body 12a, the opening 14 configured for eye observation, the opening 16 configured for intubation observation, the one or more side notches 18 configured for intubation of a patient, and strap 20. The head rest 80 comprises the strap receiving member 82, the viscoelastic foam layer 84, and the hollowed out area 92. The strap 20 of the face mask 10a is configured to attach to the strap receiving member 82 to hold the face mask 10a in place over a patient's head. The strap 20 and the strap receiving member 82 may comprise hook and loop arrangements, magnets, snaps, adhesives, or other fasteners.

Figure 16:
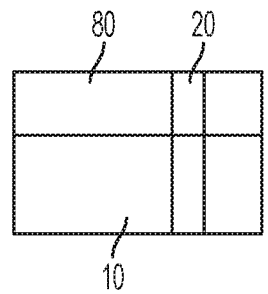
FIG. 16 is a diagram of another possible embodiment of the patient protection system of the present application for use during robotic surgery or a medical procedure, for example, such as back surgery.

FIG. 16 is a diagram of another embodiment of the patient protection system of the present application for use during robotic surgery or a medical procedure, for example, such as back surgery. The face mask portion 10 of the patient protection system is disposed below head portion 70, so that the patient can lie in the prone position, i.e. face down, with the patient's face in the face mask portion 10 and the back of the head portion 70 disposed above and on top of the back of the patient's head. The back of the head portion 70 may comprise a hard plastic covering to protect the back of the patient's head from robotic instruments. The strap 20 is configured and disposed to attach the back of the head portion 70 to the face mask 10.

Figure 17:
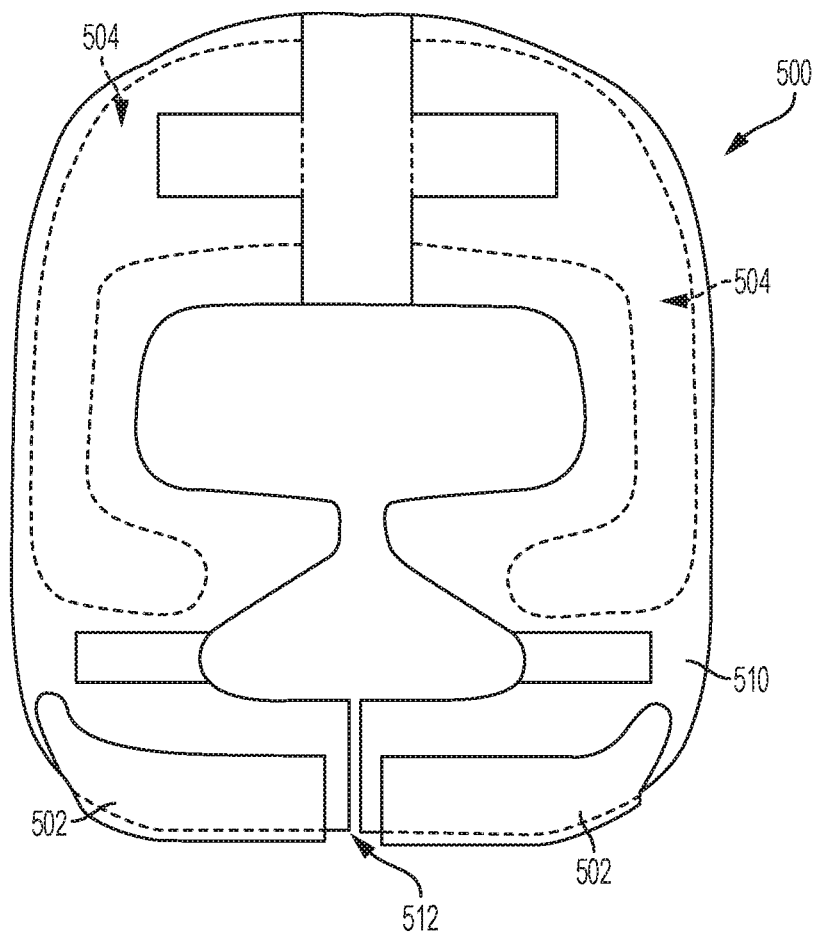
FIG. 17 shows a front view of an embodiment of a mask with protection plates affixed and embedded protection plates inserted within the mask.

In FIG. 17, an embodiment of mask 500 is shown with one or more protection plates 502 affixed in place and embedded protection plates 504 inserted within the mask 500. One or more protection plates 502 may be affixed by gluing, mechanical fastening, or by another mechanism known in the art. In embodiments, protection plates 502 and embedded protection plates 504 may comprise a plastic material. Plates 502 and 504 may also comprise metal, ceramic, polymer, or any other material known in the art. Embodiments of body 510 of mask 500 may be comprised of a foam, polyurethane, or other material known in the art. A chin area channel 512 may be included in body 510 in order to ease intubation during a surgical procedure.

Figure 18:
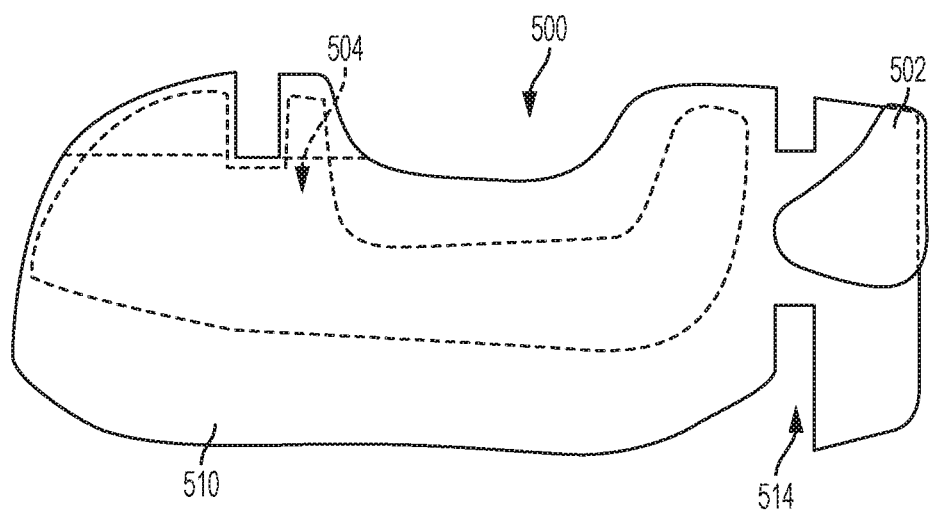
FIG. 18 shows a side view of an embodiment of a mask with the protection plates affixed and the embedded protection plates inserted within the mask.

In FIG. 18, an embodiment of mask 500 is shown from the side with the plastic protection plates 502 glued in place and the embedded protection plates 504 inserted within the mask 500. One or more intubation notches 514 may be included in body 510 in order to ease intubation during a surgical procedure.

In FIG. 19, the mask 500 is shown from the bottom side with the plastic protection plates 502 affixed in place.

FIG. 20 shows a back view of an embodiment of mask 500. In FIG. 20, foam relief pads 506a-506e are positioned within the inside of embodiments of mask 500. In an embodiment, one or more foam relief pads 506a-506e may comprise a viscoelastic foam which is softer than the viscoelastic foam of the mask 500. Foam relief pads 506a-506e may support mask 500 on a patient's face, and may provide more comfort than the material comprising body 510. In an embodiment, mask 500 also may include a depression 520 configured to receive the chin of a patient. In an embodiment, relief pads 506a and 506b may be positioned within chin depression 520.

In FIG. 21, an embodiment of embedded protective plates 504 is shown away from body 510 of mask 500.

FIG. 22 shows a side view of the embodiment of embedded protective plates 504 of FIG. 41.

FIG. 23 shows a front view of an embodiment of the mask 1000 wherein the protection plates 1002 and 1003 are affixed to the surface of the mask 1000. As with other embodiments of protection plates 504 and 502, these plates may be comprised of materials including, but not limited to, hard plastic, polymers, metal, or ceramic, and may be affixed to the surface of the mask 1000 by means of, or in other manners known in the art. An embodiment in which protection plates 1002 and 1003 are affixed to the surface of the mask includes an added advantage in that, if a robotic arm strikes the surface of the plates, a louder sound may be created than if the arm were to strike a surface made out of viscoelastic foam, non-viscoelastic polyurethane foam, or other, softer material.

FIG. 24 shows a side view of the embodiment of mask 1000 depicted in FIG. 23. One or more side channels 1004 is visible in this Figure.

An inside portion of mask 1000 may comprise foam relief pads 506a-506e, as shown in FIG. 20.

The embodiment of mask 1000 in FIG. 23 also comprises a chin area channel 1001. Like side channels 1004, and side notch 18 illustrated in FIG. 3, chin area channel 1001 may be used by operating room personnel to intubate the patient. Chin area channel 1001 may be secured with a chin strap 1007. In an embodiment, chin strap 1007 may comprise a hook portion 1008 and a loop portion 1009, as shown in FIGS. 25-27. Additional detail of an embodiment the chin strap 1007 is illustrated in FIG. 25-27. One or more of said hook and loop portions 1008 and 1009 may be affixed to the mask 1000 or chin protection plates 1003 by means of adhesives, ultrasonic welding, or other methods known in the art. Chin area channel 1001 also may be secured by means of snap closures, or other means known in the art.

An embodiment of mask 1000 illustrated in FIG. 23 also may include an eye shield 1200. Eye shield 1200 may be comprised of a transparent or translucent plastic or polymer, such as—but not limited to—polyethylene. Eye shield 1200 may be configured so that it is removable, or non-removable. In an embodiment, eye shield 1200 may be affixed in a manner that allows it to be opened or closed at the discretion of operating room personnel. In one such embodiment, shown in FIG. 23, eye shield 1200 is affixed to one side of mask 1000 with adhesive, and to the other side by means of a hook and loop mechanism 1201, and may be opened and closed. In embodiments, eye shield 1200 may by adhesive tape. Eye shield 1200 protects or substantially protects a patient's eyes during a surgical procedure, and may have rounded corners. Additionally or alternatively, the edges of eye shield 1200 may be covered with a protective material or coating.

An embodiment of mask 1000 illustrated at FIG. 23 may be secured to a patient or to a head rest by means of two straps. In an embodiment, top strap 1101 affixes to forehead channel 1006, and bottom strap 1102 affixes roughly at cheek portions 1010 of mask 1000 or protection plate 1002. In an embodiment, straps 1101 and 1102 comprise a loop material, and affix to hook portions 1103 and 1104 positioned in the forehead channel 1006 and the cheek portions of the mask 1000, respectively. In an embodiment, one or more straps 1101 and or 1102 may also comprise hook portions, so that they may affix to their own loop portions.

FIG. 28 shows an embodiment of mask 1000 affixed to a head rest 1300 by means of top strap 1101 and bottom strap 1102. In an embodiment, both straps 1101 and 1102 comprise loop material. A first end of top strap 1101 removably affixes to hook portions 1103 disposed in forehead channel 1006, wraps around mask 1000 and headrest 1300. Top strap 1101 removably attaches to itself around headrest 1300 and mask 1000 with hook portions included on a second end of top strap 1101. In another embodiment, both ends of top strap 1101 may attach to hook portions attached to the mask 1000.

In an embodiment shown in FIG. 28, bottom strap 1102 removably attaches to hook portions 1103 disposed on cheek portions 1010 of mask 1000 or protection plate 1002, and wrap around head rest 1300.

FIG. 29 illustrates a top view of an embodiment of mask 1000 removably affixed to head rest 1300 by means of straps 1101 and 1102. In this Figure, mask 1000 is superimposed over head rest 1300.

The viscoelastic foam of the present application may be a polyurethane foam made by mixing polyhydroxy polyol with toluene di-isocyanate or other and different methods as are known in the art. For example, Toluene di-isocyanate may be used in combination with polyester polyols and polyether to make viscoelastic foam.

The headrest and face mask of the present application can be used in conjunction with the METHOD OF SECURING A PATIENT ONTO AN OPERATING TABLE WHEN THE PATIENT IS IN THE TRENDELENBURG POSITION AND APPARATUS THEREFOR INCLUDING A KIT, U.S. Pat. No. 8,464,720, U.S. patent application Ser. No. 13/737,552, filed on Jan. 9, 2013, having inventors Alessio PIGAZZI and Glenn KEILAR, and U.S. Pat. No. 8,511,314, U.S. patent application Ser. No. 13/773,290, filed on Feb. 21, 2013, having inventors Alessio PIGAZZI and Glenn KEILAR.

The components disclosed in the patents, patent applications, patent publications, and other documents disclosed or incorporated by reference herein, may possibly be used in possible embodiments of the present invention, as well as equivalents thereof.

The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

International Patent Application No. PCT/US2013/020824, filed on Jan. 9, 2013, having inventors Alessio PIGAZZI and Glenn KEILAR, and title METHOD OF SECURING A PATIENT ONTO AN OPERATING TABLE WHEN THE PATIENT IS IN THE TRENDELENBURG POSITION AND APPARATUS THEREFOR INCLUDING A KIT, is hereby incorporated by reference as if set forth in its entirety herein.

An example of a robotic surgery system, such as the Da Vinci Surgical System, is made by Intuitive Surgical, Inc., located at 1266 Kifer Road #101, Sunnyvale, Calif. 94086.

U.S. Pat. No. 8,066,524, having the title SURGICAL SYSTEM WITH ELECTRO-MECHANICAL INTERFACES TO MOUNT ROBOTIC SURGICAL ARMS, issued on Nov. 29, 2011, is hereby incorporated by reference as if set forth in its entirety herein.

Kevlar® is a registered trademark for a para-904 aramid synthetic fiber registered to DuPont, headquartered at 1007 Market Street, 906 Wilmington, Del. 19898, USA. Some examples of Kevlar® which may possibly be utilized in at least one possible embodiment of the present application, may possibly be found in the following U.S. Pat. No. 8,302,213, having the title "Helmets and vests," issued on Nov. 6, 2012; and U.S. Pat. No. 4,574,105, having the title "Penetration resistant textile panels with plies of nylon and plies of Kevlar," issued on Mar. 4, 1986.

Some examples of viscoelastic foam, which may possibly be utilized in at least one possible embodiment of the present application, may possibly be found in the following U.S. Pat. No. 7,078,443, having the title "Viscoelastic foam layer and composition," issued on Jul. 18, 2006; U.S. Pat. No. 8,399,085, having the title "Energy-absorbing pads," issued on Mar. 19, 2013; U.S. Pat. No. 8,359,689, having the title "Mattress adapted for supporting heavy weight persons," issued on Jan. 29, 2013; U.S. Pat. No. 7,789,461, having the title "Seating accessory," issued on Sep. 7, 2010; U.S. Pat. No. 6,895,619, having the title "Foldable pillow," issued on May 24, 2005; and U.S. Pat. No. 6,453,476, having the title "Protective helmet," issued on Sep. 24, 2002, which are hereby incorporated by reference into this application.

Some examples of polyethylene foam, which may possibly be utilized in at least one possible embodiment of the present application, may possibly be found in the following U.S. patents: U.S. Pat. No. 6,245,266, having the title "Method for making oriented polyethylene foam and foam produced thereby", issued on Jun. 12, 2001; U.S. Pat. No. 5,206,082, having the title "Nondistorted polyethylene foam structures and process for making", issued on Apr. 27, 1993; U.S. Pat. No. 4,877,814, having the title "Process for producing open-cell polyethylene foam materials and the resultant product", issued on Oct. 31, 1989; U.S. Pat. No. 4,719,039, having the title "Electrically conductive polyethylene foam," issued on Jan. 12, 1988; U.S. Pat. No. 4,220,730, having the title "Crosslinked chlorinated polyethylene foam", issued on Sep. 2, 1980; and U.S. Pat. No. 4,209,473, having the title "Crosslinked chlorinated polyethylene foam", issued on Jun. 24, 1980, all of which are hereby incorporated by reference into this application.

Some examples of polypropylene foam, which may possibly be utilized in at least one possible embodiment of the present application, may possibly be found in the following U.S. patents: U.S. Pat. No. 7,799,841, having the title "Polypropylene foam", issued on Sep. 21, 2010; U.S. Pat. No. 7,759,404, having the title "Inherently open celled polypropylene foam with large cell size", issued on Jul. 20, 2010; U.S. Pat. No. 6,773,796, having the title "Thermoformable multi-layer polypropylene foam sheet", issued on Aug. 10, 2004; U.S. Pat. No. 5,567,742, having the title "Dimensionally-stable polypropylene foam expanded with inorganic blowing agents", issued on Oct. 22, 1996; U.S. Pat. No. 5,527,573, having the title "Extruded closed-cell polypropylene foam", issued on Jun. 18, 1996; and U.S. Pat. No. 5,180,751, having the title "Polypropylene foam sheets", issued on Jan. 19, 1993, all of which are hereby incorporated by reference into this application.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

It is to be understood that the invention may assume various alternative variations, except where expressly specified to the contrary. It is also to be understood that the specific devices illustrated in the attached drawings, and described in the specification, are simply exemplary embodiments of the invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope thereof. For example, it is to be understood that the present invention contemplates that, to the extent possible, one or more features of any embodiment can be combined with one or more features of any other embodiment. The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

The invention claimed is:

1. A patient protection system configured for protecting a patient's face and eyes during a surgical procedure, the system comprising:
    a face mask structure comprising a foam body having an exterior surface and an interior surface configured to be oriented towards the patient's face to cover the patient's face during the surgical procedure; and
    at least one foam pad positioned on the interior surface of the face mask structure and configured to contact the patient's face during the surgical procedure,
    wherein the face mask structure and the at least one foam pad are manufactured from different types of foam,
    wherein the face mask structure is manufactured from a first type of foam and the at least one foam pad is manufactured from a viscoelastic foam that is softer than the first type of foam and
    wherein the face mask structure further comprises one or more side notches configured to be aligned with the patient's mouth and configured to allow intubation of the patient during robotic surgery.

2. The patient protection system of claim 1, further comprising a head rest unit configured to contact and support a head of the patient during the surgical procedure,
    wherein the head rest unit is comprised of a foam material.

3. The patient protection system of claim 2, wherein the head rest unit further comprises one or more strap receiving members formed on an exterior surface thereof;
    wherein the one or more strap receiving members are configured to coact with one or more straps of the face mask structure to secure the face mask structure during robotic surgery.

4. The patient protection system of claim 1, wherein the at least one foam pad includes at least one first foam pad positioned on the interior surface of the face mask structure to come into contact with a chin of the patient and at least one second foam pad positioned on the interior surface of the face mask structure to come into contact with a forehead of the patient.

5. The patient protection system of claim 1, wherein the face mask structure further comprises:
    an eye opening configured to allow observation of the patient's eyes during the surgical procedure.

6. The patient protection system of claim 1, wherein the face mask structure further comprises an intubation observation opening formed on the exterior surface thereof and extending through the interior surface and configured to allow observation of an intubation of the patient during the surgical procedure.

7. The patient protection system of claim 1, further comprising a strap operatively connected to the face mask structure and configured to secure the face mask structure to the patient during the surgical procedure.

8. The patient protection system of claim 1 further comprising one or more plate members affixed to the exterior surface of the face mask structure.

9. The patient protection system of claim 1, wherein the one or more side notches are about one inch long, and span a width of the face mask structure.

10. The patient protection system of claim 1, wherein the facemask structure comprises at least one rounded corner.

11. A face mask for use during a surgical procedure, comprising:
    a foam body comprising an exterior surface and an interior surface configured to cover a face of a patient during the surgical procedure;
    at least one foam pad positioned on the interior surface of the foam body and configured to contact the patient's face during the surgical procedure,
    wherein the foam body is manufactured from a first type of foam and the at least one foam pad is manufactured from a viscoelastic foam that is softer than the first type of foam;
    a chin area channel extending from the exterior surface to the interior surface of the foam body at a bottom area of the foam body and configured to allow intubation of the patient during the surgical procedure;
    one or more side notches configured to be aligned with the patient's mouth and configured to allow intubation of the patient during the surgical procedure; and
    a fastener provided on the exterior surface of the foam body in the bottom area of the foam body and configured to allow opening and closure of the chin area channel during the surgical procedure.

12. The face mask of claim 11, further comprising an eye opening formed in the exterior surface of the foam body and configured to allow observation of the patient's eyes during robotic surgery.

13. The face mask of claim 12, further comprising:
    an eye shield positioned over the eye opening and configured to cover the patient's eyes and to allow observation of the patient's eyes during the surgical procedure; and
    one or more fasteners configured to removably attach the eye shield to the foam body over the eye opening.

14. The face mask of claim 13, wherein the one or more fasteners configured to removably attach the eye shield is at least one of a hook and loop arrangement, one or more magnets, snaps, or an adhesive.

15. The face mask of claim 11, further comprising:
    one or more plate members positioned on the exterior surface of the foam body and configured to protect the patient during the surgical procedure.

16. The face mask of claim 15, wherein the one or more plate members comprise:
    one or more protection plates positioned on the foam body to protect a forehead of the patient and a side of the patient's face; and
    one or more chin protection plates positioned on the foam body to protect a chin of the patient.

17. The face mask of claim 11, wherein the at least one foam pad is positioned on the interior surface of the foam body and configured to contact the patient's face during the surgical procedure.

18. The face mask of claim 11, wherein the fastener provided on the exterior surface of the foam body is at least one of a hook and loop arrangement, one or more magnets, snaps, or an adhesive.

19. A method for protecting a face of a patient during a surgical procedure comprising:
  placing a patient's head on a head rest unit configured to support the patient's head;
  placing a face mask structure configured to protect the patient's face over the patient's face, the face mask structure comprising:
    a foam body having an exterior surface and an interior surface configured to be oriented towards the patient's face to cover the patient's face during the surgical procedure;
    at least one foam pad positioned on the interior surface of the face mask structure and configured to contact the patient's face during the surgical procedure;
    one or more side notches configured to be aligned with the patient's mouth and configured to allow intubation of the patient during the surgical procedure; and
  securing the face mask structure to the head rest unit, wherein the face mask structure is manufactured from a first type of foam and the at least one foam pad is manufactured from a viscoelastic foam that is softer than the first type of foam.

20. The method of claim 19, wherein the face mask structure further comprises a chin area channel extending from the exterior surface to the interior surface of the foam body at a bottom area of the foam body; and the method further comprises intubating the patient and positioning an intubation tube within the chin area channel.

21. The method of claim 19, wherein the face mask structure further comprises an eye shield positioned over an eye opening formed in the foam body, the eye shield configured to cover a patient's eyes and to allow observation of the patient's eyes during the surgical procedure; and one or more fasteners configured to removably attach the eye shield to the foam body; and the method further comprises closing and removably securing the eye shield in place.

* * * * *

UNITED STATES PATENT AND TRADEMARK OFFICE
CERTIFICATE OF CORRECTION

PATENT NO. : 10,842,206 B2
APPLICATION NO. : 15/019454
DATED : November 24, 2020
INVENTOR(S) : Kaforey et al.

Page 1 of 1

It is certified that error appears in the above-identified patent and that said Letters Patent is hereby corrected as shown below:

In the Specification

Column 2, Line 43, delete "configured to coact with" and insert -- configured to contact with --

In the Claims

Column 17, Line 46, Claim 3, delete "configured to coact with" and insert -- configured to contact with --

Column 18, Line 10, Claim 10, delete "facemask" and insert -- face mask --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*